US00PP13991P29

(12) United States Plant Patent
Turner

(10) Patent No.: US PP13,991 P2
(45) Date of Patent: Jul. 22, 2003

(54) BRACTEANTHA PLANT NAMED 'YELLOW'

(75) Inventor: Matthew Turner, Penrith South (AU)

(73) Assignee: Oasis Horticulture Pty. Ltd. (AU)

( * ) Notice: Subject to any disclaimer, the term of this patent is extended or adjusted under 35 U.S.C. 154(b) by 0 days.

(21) Appl. No.: 10/109,514

(22) Filed: Mar. 27, 2002

(51) Int. Cl.[7] ..... A01H 5/00
(52) U.S. Cl. ..... Plt./359
(58) Field of Search ..... Plt./359

(56) References Cited

U.S. PATENT DOCUMENTS

PP11,800 P2 * 3/2001 Bautista ..... Plt./359

* cited by examiner

*Primary Examiner*—Bruce R. Campell
*Assistant Examiner*—Susan B. McCormick
(74) *Attorney, Agent, or Firm*—Wood, Phillips, Katz, Clark & Moritmer

(57) ABSTRACT

A new and distinct Bracteantha plant named 'Yellow', characterized by its yellow involucral bracts, yellow disc florets, upright mounded growth habit, and dark green leaves.

1 Drawing Sheet

LATIN NAME OF THE GENUS AND SPECIES OF PLANT CLAIMED

*Bracteantha bracteata.*

VARIETY DEMONINATIION

'Yellow'.

BACKGROUND OF THE INVENTION

The present invention comprises a new and distinct Bracteantha plant, botanically know as *Bracteantha bracteata* and hereinafter referred to by the cultivar name 'Yellow'.

The new cultivar was developed by the inventor through a controlled breeding program Mar. 1, 1998, at New South Wales, Australia.

The female (seed) parent of 'Yellow' was the cultivar 'Nullabor Flame' (not patented in the United States) characterized by it tall habit and large numbers of bracts. The male (pollen) parent of 'Yellow' was the cultivar 'Diamond Head' (not patented in the United States) characterized by its semi-prostrate habit and low number of bracts. 'Yellow' was selected as one of the flowering progeny of the above cross Aug. 1, 1998.

Asexual reproduction of the new cultivar by terminal cuttings, at West Chicago, Ill., has demonstrated that the characteristics of the new cultivar as herein described are firmly fixed and retained through successive generations of such asexual propagation.

SUMMARY OF THE INVENTION

It was found that the cultivar of the present invention:

(a) Exhibits yellow involucral bracts and yellow disc florets;

(b) forms dark green foliage;

(c) exhibits a good basal branching character; and (d) exhibits an upright mounded growth habit.

When the new cultivar of the present invention is compared to 'Cream' (disclosed in U.S. Plant patent application Ser. No. 09/819,340) it is found that the new cultivar has slightly smaller leaves and slightly smaller flowers of a darker yellow color. The new cultivar can also be compared to 'Gold 'N' Bronze' (U.S. Plant Pat. No. 10,193). However, in side by side comparisons, the new cultivar has lighter bract color. When compared to its sibling, 'Copper', the new cultivar has much lighter bract color.

BRIEF DESCRIPTION OF PHOTOGRAPH

The accompanying photograph show as nearly true as it is reasonably possible to make the same in color illustrations of this type, typical flower and foliage characteristics of the new cultivar. The photograph illustrates two plants in one pot, grown for 10 weeks in a greenhouse at West Chicago, Ill.

DETAILED BOTANICAL DESCRIPTION

The Yellow cultivar has not been observed under all possible environmental conditions to date. Accordingly, it is possible that the phenotype may vary somewhat with variations in the environment, such as temperature, light intensity, and day length.

The chart used in the identification of colors described herein is The R.H.S. Colour Chart of The Royal Horticultural Society, London, England. The color values were determined on Feb. 15, 2002. The readings were taken between 10:00 and 11:00 a.m. under natural daylight conditions. The plants were produced from cuttings taken from stock plants and were grown for 12 weeks in a double polycarbonate covered greenhouse under conditions comparable to those used in commercial practice while utilizing a soilless growth medium. Temperatures of approximately 65° to 75° (18° to 24° C.) during the day and approximately 55° to 60° F. (13° to 16° C.) during the night and light levels of between 5,000 and 8,000 footcandles were maintained.

Classification:
*Botanical.*—*Bracteantha bracteata*, cultivar 'Yellow'.
*Commercial.*—Helichrysum.

Parentage:
*Female parent.*—'Nullabor Flame'.
*Male parent.*—'Diamond Head'.

Propagation:
*Type cutting.*—Terminal tip.

*Time to initiate roots.*—Approximately 21 to 30 days with the shorter times generally being experienced in the summer and the longer times in the winter.

Plant description:

*Form.*—Upright, mounded.

*Habit of growth.*—Moderate. A mature plant, 12 weeks after the planting of a rooted cutting, commonly measures approximately 15.2 cm in height and approximately 41 8 cm in diameter.

*Branching habit.*—Freely basal branching although pinching improves basal branching. Commonly develops approximately 5 lateral branches.

*Lateral branch.*—Length: Approximately 19.4 cm. Diameter: Approximately 5 mm with hirsute pubescence. Color: 145B. Internode length: Approximately 6 mm.

*Foliage.*—Arrangement: Alternate. Shape: Linear with entire margin, acute apex and clasping base. Size: Approximately 4.8 cm in length and approximately 6 mm at widest point. Upper surface is rough and 137A. Lower surface is smooth 137C. Midvein on lower surface is moderately pubescent. Venation of both surfaces: Closest to 144C.

Flowering description:

*Flowering habit.*—Freely flowering.

*Natural flowering season.*—Spring through fall.

Flower description:

*Inflorescence type.*—Single, composite.

*Bud.*—Size: 2 cm in length, 1.9 cm in diameter. Color: 168B at tip and 162D at base.

*Inflorescence diameter.*—Approximately 3.6 cm.

*Involucral bracts.*—Quantity: Approximately 106, arranged in 10 whorls. Aspect: Appear flat at maturity then become downwardly pointing with age. Texture: Smooth, papery. Shape: Linear. Size: Length — 1.4 cm, width varies from 1 mm (inner whorl) to 4 mm (outer whorl). Color — Upper surface, fully opened: Outer 2 (two) whorls are 14A with 170A at tip; 3$^{rd}$ whorl is 14A with 23A at tip; inner whorls are 14A. Lower surface: 168B at tip and 162D at base.

*Disc diameter.*—1.2 cm.

*Disc florets.*—Shape: Tubular. Length: Approximately 1.2 cm.

*Peduncle.*—Length: Approximately 5 cm. Diameter: Approximately 2 mm. Strength: Good. Aspect: Erect. Color: 146B. Texture: Puberulent.

*Fragrance.*—None.

*Reproductive organs.*—Androecium — Stamen number: 1. Anther color: 24A Pollen color: 21A. Gynoecium: Pistil number: 1. Pistil length: 9 mm. Stigma shape: Bilobate. Stigma color: 20A. Style length: Approximately 4 mm. Style color: 1B.

Disease resistance: Resistance to diseases common to Helichrysum has not been observed.

Seed development: Seed development has not been observed.

I claim:

1. A new and distinct cultivar of Bractheantha plant named 'Yellow' substantially as herein shown and described, which:

(a) exhibits yellow involucral bracts and yellow disc florets;

(b) forms dark green foliage;

(c) exhibits a good basal branching character; and (d) exhibits an upright mounded growth habit.

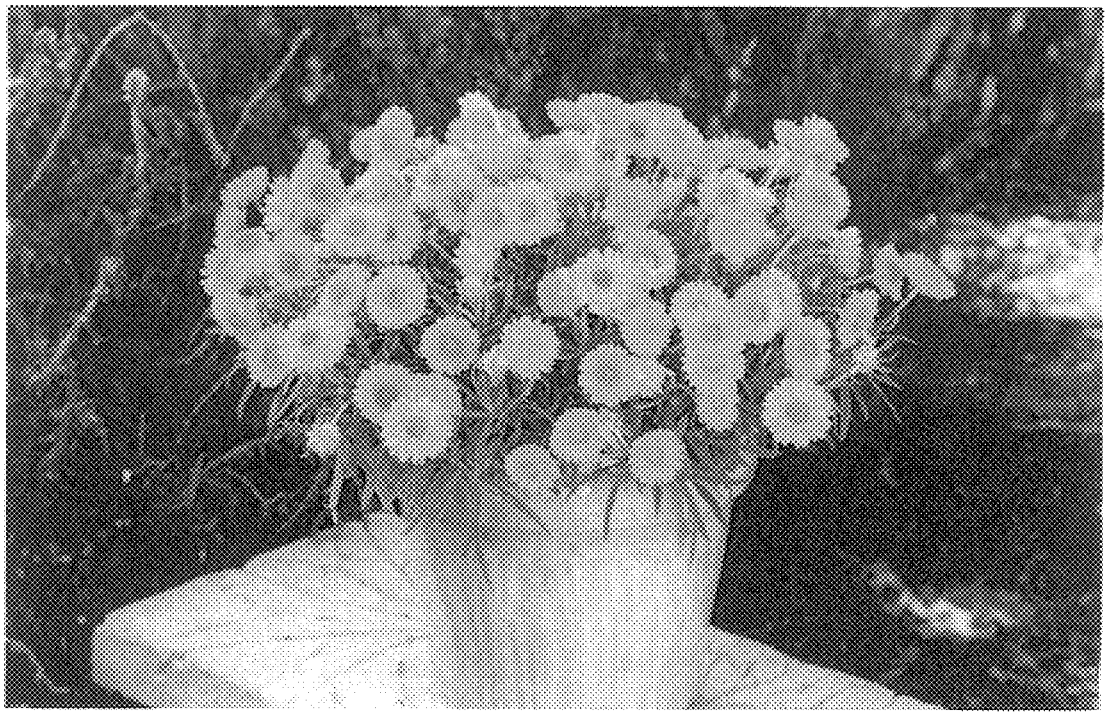

* * * * *